US006808938B2

(12) United States Patent
Hämäläinen et al.

(10) Patent No.: US 6,808,938 B2
(45) Date of Patent: Oct. 26, 2004

(54) METHOD AND APPARATUS FOR ASSAYING A DRUG CANDIDATE TO ESTIMATE A PHARMACOKINETIC PARAMETER ASSOCIATED THEREWITH

(75) Inventors: Markku Hämäläinen, Uppsala (SE); Robert Karlsson, Uppsala (SE); Stefan Löfås, Uppsala (SE)

(73) Assignee: Biacore AB, Uppsala (SE)

( * ) Notice: Subject to any disclaimer, the term of this patent is extended or adjusted under 35 U.S.C. 154(b) by 368 days.

(21) Appl. No.: 09/921,496

(22) Filed: Aug. 3, 2001

(65) Prior Publication Data

US 2002/0019019 A1 Feb. 14, 2002

Related U.S. Application Data

(63) Continuation of application No. 09/336,865, filed on Jun. 18, 1999, now abandoned.

(51) Int. Cl.$^7$ ............................................. G01N 33/543
(52) U.S. Cl. ..................... 436/518; 385/12; 385/129; 385/130; 356/418; 422/82.11; 435/7.1; 435/7.2; 435/7.4; 436/164; 436/165; 436/524; 436/525; 436/527; 436/528; 436/529; 436/805
(58) Field of Search ............................. 435/7.1, 7.2, 7.4, 435/282.1, 282.2, 288.7, 808; 436/164, 165, 518, 524, 525, 527, 528, 529, 805; 385/12, 129, 130; 422/87.11; 356/418

(56) References Cited

U.S. PATENT DOCUMENTS

| 5,242,828 | A | 9/1993 | Bergström et al. ........... 435/291 |
| 5,313,264 | A | 5/1994 | Ivarsson et al. ............... 356/73 |
| 5,338,659 | A | 8/1994 | Kauvar et al. ................ 435/7.1 |
| 5,436,161 | A | 7/1995 | Bergström et al. ........... 435/291 |
| 5,485,277 | A | 1/1996 | Foster ......................... 356/445 |
| 5,492,840 | A | 2/1996 | Malmqvist et al. .......... 436/518 |
| 5,554,541 | A | 9/1996 | Malmqvist et al. .......... 436/518 |
| 5,620,850 | A | 4/1997 | Bamdad et al. .............. 530/300 |
| 5,716,854 | A | 2/1998 | Löfås et al. ................. 436/518 |
| 5,955,729 | A | 9/1999 | Nelson et al. ............... 250/282 |
| 6,651,008 | B1 * | 11/2003 | Vaisberg et al. .............. 702/21 |

FOREIGN PATENT DOCUMENTS

| WO | WO 97/09618 | 3/1997 |
| WO | WO 99/63333 | 12/1999 |

OTHER PUBLICATIONS

Cook et al., "Effect of Salcylic Acid on the Plasma Protein Binding and Pharmacokinetics of Misoprostol Acid," *Journal of Pharmaceutical Sciences* 83(6):883–886, Jun. 1994.
Gex–Fabry et al., *Pharmacokinetics of Drugs*, Springer–Verlag, New York, 1994, Chapter 18, "Considerations on Data Analysis Using Computer Methods and Currently Available Software for Personal Computers," pp. 507–527.

Giorgio et al., "Pharmacokinetics in a Phase I Study of a Chimerized Monoclonal–epidermal Growth Factor Receptor (EGFr) Antibody C225, as Determined by Surface Plasmon Resonance," in *87$^{th}$ Annual Meeting of the American Association for Cancer Research*, Proceedings of the American Association for Cancer Research, New York, Apr. 22, 1996, vol. 37, Mar. 1996, #1230, pp. 180.
Gomeni, "Pharm–An Interactive Graphic Program for Individual and Population Pharmacokinetic Parameter Estimation," *Comput. Biol. Med.* 14(1):25–34, 1984.
Kansy et al., "Physicochemical High Throughput Screening: Parallel Artifical Membrane Permeation Assay in the Description of Passive Absorption Processes," *Journal of Medicinal Chemistry* 41(7): 1007–1010, Mar. 26, 1998.
Keller et al., Standardized Structure and Modular Design of a Pharmacokinetic Database, *Computer Methods and Programs in Biomedicine* 55:107–115, 1998.
Kubota and Ishizaki, "A Diffusion–Diffusion Model for Percutaneous Drug Absorption," *Journal of Pharmacokinetics and Biopharmaceutics* 14(4):409–439, 1986.
Löfås and Johnsson, "A Novel Hydrogel Matrix on Gold Surfaces in Surface Plasmon Resonance Sensors for Fast and Efficient Covalent Immobilization of Ligands," *J. Chem. Soc. Chem. Commun.* 21:1526–1528, 1990.
Lundström, "Real–time Biospecific Interaction Analysis," *Biosensors & Bioelectronics* 9:725–736, 1994.
Madaras–Kelly et al., "Twenty–Four–Hour Area under the Concentration–Time Curve/MIC Ratio as a Generic Predictor of Fluoroquinolone Antimicrobial Effect by Using Three Strains of *Pseudomonas aeruginosa* and an In Vitro Pharmacodynamic Model," *Antimicrobial Agents and Chemotherapy* 40(3):627–632, Mar. 1996.

(List continued on next page.)

Primary Examiner—Christopher L. Chin
(74) Attorney, Agent, or Firm—Seed IP Law Group PLLC

(57) ABSTRACT

A method and apparatus for assaying a drug candidate with a biosensor having one or more sensing surface-bound biomolecules associated therewith are disclosed. The method comprises the steps of measuring the binding interaction between the drug candidate and the one or more sensing surface-bound biomolecules of the biosensor to obtain an estimate of at least one binding interaction parameter of the drug candidate, and then comparing the estimated binding interaction parameter against a mathematical expression correlated from binding interaction data associated with known drug compounds to determine an estimate of at least pharmacokinetic parameter of absorption, distribution, metabolism, or excretion (ADME) that is related to the drug candidate. The present invention allows for the simultaneous measurement of different pharmacokinetic parameters of the drug candidate, as well as an indication of the drug candidate's solubility, by use of a single analytical instrument. The pharmacokinetic data may be represented as a ADME characterization profile; such ADME profiles are of great utility for purposes of drug screening and lead optimization.

19 Claims, 8 Drawing Sheets

OTHER PUBLICATIONS

Majamdar, "Characterization of the Dose–Dependent Time of Peak Effect in Indirect Response Models," *Journal of Pharmacokinetics and Biopharmaceutics,* 26(2): 183–206, 1998.

Pacifici and Viani, "Methods of Determining Plasma and Tissue Binding of Drugs," *Clinical Pharmacokinetic Concepts* 23(6):449–468, 1992.

Pelkonen and Breimer, "Role of Enviromental Factors in the Pharmacokinetics of Drugs: Considerations with Respect to Animal Models, P–450 Enzymes, and Probe Drugs," in Welling and Balant (eds), *Pharmacokinetics of Drugs,* Springer–Verlag, New York, 1994, pp. 287–332.

Podczeck et al., "The Assessment of Pharmacokinetic Parameters of Teicoplanin in Burns Comparing the Methods of Nonlinear Curve Fitting and Quantified Maximum Entropy," *International Journal of Pharmaceutics* 142:235–246, 1996.

Purves, "Numerical Estimation of the Noncompartmental Pharmacokinetic Parameters Variance and Coefficient of Variation of Residence Times," *Journal of Pharmacetical Sciences* 83(2):202–205, Feb. 1994.

Rowland, "Kinetics of Drug–Drug Interactions," in Teorell et al. (eds), *Pharmacology and Pharmacokenetics,* Plenum Press, 1975, pp. 321–337.

Shek et al., "Distribution of Free and Liposomal Cefoxitin in Plasma and Peritoneal Fluid in a Porcine Intra–abdominal Sepsis Model," *Journal of Drug Targeting* 5(5):353–364, 1998.

Singvi, "Estimation of Pharmacokinetic Parameters from Postinfusion Blood Level Data Obtained after Simultaneous Administration of Intravenous Priming and Infusion Doses," *Journal of Pharmacetical Sciences* 66(10):1499–1501, Oct. 1977.

Upton et al., "A Method for Estimating Within–Individual Variability in Clearance and in Volume of Distribution from Standard Bioavailability Studies," *Journal of Pharmacokinetics and Biopharmaceutics* 10(2):135–146, 1982.

Vogelman et al., "Correlation of Antimicrobial Pharmacokinetic Parameters with Therapeutic Efficacy in an Animal Model," *The Journal of Infectious Disease* 158(4):831–847, Oct. 1988.

Yacabi and Levy, "Comparative Pharmacokinetics of Coumarin Anticoagulants XXI: Effects of Plasma Protein Binding on Distribution Kinetics of Warfarin in Rats," *Journal of Pharmacetical Sciences* 66(4):567–572, Apr. 1977.

Yamaguchi et al., "Research to Develop a Predicting System of Mamalian Subacute Toxicity (3) Construction of a Predictive Toxicokinetics Model," *Chemosphere* 33(12):2441–2468, 1996.

Yokel, "Benefit vs. risk of oral aluminum forms: antacid and phosphate binding vs. absorption," *Drug and Chemical Toxicology* 12(3–4):277–286, 1989.

* cited by examiner

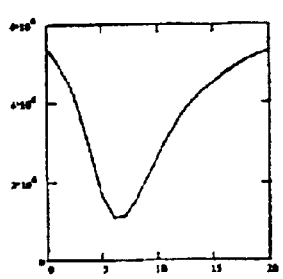 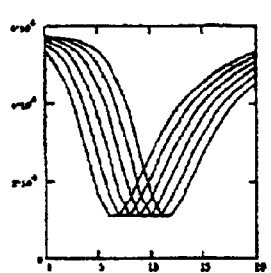 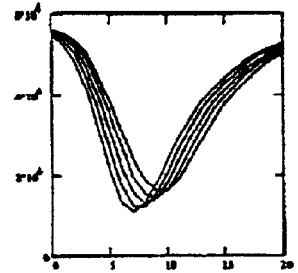
*Fig. 2a*    *Fig. 2b*    *Fig. 2c*

METHOD AND APPARATUS FOR ASSAYING A DRUG CANDIDATE TO ESTIMATE A PHARMACOKINETIC PARAMETER ASSOCIATED THEREWITH

CROSS-REFERENCE TO RELATED APPLICATION

This application is a continuation of U.S. patent application Ser. No. 09/336,865, filed Jun. 18, 1999, now abandoned.

TECHNICAL FIELD

This invention is generally directed to a method and apparatus for assaying a drug candidate and, more specifically, to a method for measuring the binding interaction between a drug candidate and sensing surface-bound biomolecules of a biosensor to determine a binding interaction parameter of the drug candidate, and then comparing the binding interaction parameter against a predetermined drug correlation graph (e.g., a mathematical expression) to estimate at least one pharmacokinetic parameter.

BACKGROUND OF THE INVENTION

A variety of experimental techniques are currently used to determine chemical, physical and biological properties associated with low molecular weight substances, particularly in the context of drug discovery. For example, researchers are often concerned with determining a variety of chemical, physical and biological properties associated with drug candidates for screening purposes. The determination of such properties often plays a pivotal role in the drug development and screening process.

More specifically, it has long been recognized that the intensity and duration of the pharmacological effect of a systemically acting drug are functions not only of the intrinsic activity of the drug, but also of its absorption, distribution, metabolism, and excretion (ADME) characteristics within the human body. These so-called ADME characteristics are all intimately related to the scientific discipline known as "pharmacokinetics." Pharmacokinetics is commonly referred to as the study of the time courses (i.e., kinetics) associated with the dynamic processes of ADME of a drug and/or its metabolites within a living organism, and is closely interrelated with the fields of biopharmaceutics, pharmacology, and therapeutics.

Because the body delays the transport of drug molecules across membranes, dilutes them into various compartments of distribution, transforms them into metabolites, and eventually excretes them, it is often difficult to accurately predict the pharmacological effect of promising new drug candidates. Researchers, however, commonly use pharmacokinetic ADME studies as one method to predict the efficacy of a drug at a site of action within the body.

Traditionally, researchers involved with preclinical ADME studies have used pharmacokinetic/mathematical models coupled with actual drug concentration data from blood (or serum or plasma) and/or urine, as well as concentration data from various tissues, to characterize the behavior and "fate" of a drug within living organisms. As is appreciated by those skilled in the art, the mathematical equations associated with pharmacokinetics are generally based on models that conceive the body as a multicompartmental organism. In such models it is presumed that the drug and/or its metabolites are equitably dispersed in one or several fluids/tissues of the organism. Any conglomerate of fluid or tissue which acts as if it is kinetically homogeneous may be termed a "compartment." Each compartment acts as an isotropic fluid in which the molecules of drug that enter are homogeneously dispersed and where kinetic dependencies of the dynamic pharmacokinetic processes may be formulated as functions of the amounts or concentrations of drug and metabolites therein. Stated somewhat differently, the conceptual compartments of the body are separated by barriers that prevent the free diffusion of drug among them; the barriers are kinetically definable in that the rate of transport of drug or metabolite across membrane barriers between compartments is a function of, for example, the amounts or concentrations of drug and metabolites in the compartments, the permeability of various membranes, and/or the amount of plasma protein binding and general tissue binding.

More specifically, pharmacokinetic/mathematical models are commonly used by pharmacokineticists to represent drug absorption, distribution, metabolism, and excretion as functions of time within the various tissues and organs of the body. In such models, the movement of the administered drug throughout the body is concisely described in mathematical terms (e.g., a set of differential equations). The predictive capability of such models lies in the proper selection and development of mathematical functions that parameterize the essential factors governing the kinetic process under consideration.

For example, a drug that is administered by intravenous injection may be assumed to distribute rapidly in the bloodstream. A pharmacokinetic/mathematical model that describes this situation may be a tank containing a volume of fluid that is rapidly equilibrated with the drug. Because a fraction of the drug in the body is continually eliminated as a function of time (e.g., excreted by the kidneys and metabolized by the liver), the concentration of the drug in the hypothetical tank may be characterized by two parameters: (1) the volume of fluid in the tank that will dilute the drug, and (2) the elimination rate of the drug per unit of time, both of which are generally considered to be constant. Thus, if a known set of drug concentrations in the tank is determined at various time intervals by, for example, sampling, then the volume of fluid in the tank and rate of drug elimination may be estimated. This information may then, in turn, be used for predicting the disposition of the drug within a human body.

Theoretically, an unlimited number of models may be constructed to describe the kinetic processes of drug absorption, distribution, metabolism, and excretion within the various tissues and organs of the human body. In general, however, the number of useful models is limited due to practical considerations associated with blood, tissue and/or organ sampling. As a result, and as is appreciated by those skilled in the art, two major types of models have been developed by pharmacokineticists: (1) compartmental models; and (2) physiologic models.

In pharmacokinetic compartmental models, the body is represented as a series of compartments that communicate reversibly with each other. Each compartment is not a real physiological or anatomic region; rather, each compartment is considered to be inclusive of all tissues that have similar blood flow and drug affinity. For example, a compartmental model may consist of one or more peripheral compartments representing tissue(s) connected to a central compartment representing the blood stream. Conceptually, the drug moves dynamically into and out of the central compartment and into and out of each of the peripheral compartments. As such, rate constants may be used to represent the overall rate process for the drug's disposition within each compartment.

Compartment models are generally based on linear assumptions using linear differential equations, and are particularly useful when there is little information known about the tissues and their respective drug concentrations.

In contrast, pharmacokinetic physiologic models are based on known anatomic and physiologic data, data which is kinetically described in view of the actual blood flow volumes responsible for distributing the drug to the various parts of the body. Because there are many tissue organs in the body, each tissue volume must be estimated and its drug concentration and rate of change described mathematically (tissues having similar blood perfusion properties, however, are typically grouped together). Unfortunately, much of the information required to adequately describe such pharmacokinetic physiologic models are often very difficult to obtain experimentally. Nevertheless, such physiologically based models are commonly used in conjunction with animal data and interspecies scaling techniques to predict the drug's disposition within a human body.

More importantly, however, is that pharmacokinetic/mathematical models, and knowledge of their associated ADME parameters play an extremely important role in drug discovery and development. A typical example is a drug that is active following intravenous administration but is considerably less active after comparable oral doses. Having appropriate pharmacokinetic information may reveal (1) whether the drug was poorly absorbed to yield subtherapeutic circulating levels, or (2) whether the drug experienced presystemic metabolism to an inactive metabolite. Such information may also provide guidance for subsequent decisions, such as (1) whether to improve drug absorption by altering the salt form or formulation, (2) whether to investigate the possibility of making prodrugs, or (3) whether to consider a parenteral route of administration.

In addition to the foregoing, pharmacokinetic/mathematical models are also generally considered extremely useful for, among other things: (1) predicting plasma, tissue, and urine drug levels with any dosage regimen; (2) calculating the optimum dosage regimen for an individual patient; (3) estimating the possible accumulation of drugs and/or metabolites; (4) correlating drug concentrations with pharmacologic and toxicologic activity (i.e., pharmacodynamics); (5) evaluating differences in the rate or extent of availability between formulations (i.e., bioequivalence); (6) describing how changes in physiology or disease affect the absorption, distribution, and/or elimination of the drug; and (7) explaining drug-drug and food-drug interactions.

Lastly, pharmacokinetic ADME data has also become an integral part of the pharmacological characterization process of promising new drug candidates. Regulatory agencies, such as the U.S. Food and Drug Administration, now require (1) a determination of pharmacokinetic ADME data in Phase I drug studies, and (2) a submission of pharmacokinetic ADME data as part of a New Drug Application. In this context, such pharmacokinetic ADME data is deemed essential for predicting the behavior and fate of the drug candidate within the human body.

Accordingly, there is a need in the art for improved methods for determining one or more pharmacokinetic parameters associated with absorption, distribution, metabolism, and excretion of a drug candidate. There is also a need for apparatuses useful for carrying out such methods. The present invention fulfills these needs and provides further related advantages.

SUMMARY OF THE INVENTION

In brief, the present invention is directed to a method and apparatus for assaying a drug candidate. More specifically, this invention discloses a method for measuring the binding interaction between a drug candidate and sensing surface-bound biomolecules of a biosensor to determine a binding interaction parameter of the drug candidate, and then comparing the binding interaction parameter against a predetermined drug correlation graph to estimate at least one pharmacokinetic parameter of the drug candidate. The at least one pharmacokinetic parameter may, for example, be one or more of ADME.

In another embodiment of the present invention, at least two pharmacokinetic parameters of the drug candidate are determined, and in yet another embodiment, at least one pharmacokinetic parameter and a solubility property of the drug candidate are determined. Such pharmacokinetic parameters and/or solubility property may be determined when the one or more sensing surface-bound biomolecules are selected from, for example, liposomes, plasma proteins, CYP 450 enzymes, metabolic enzymes, or transport proteins.

The biosensor used in the practice of the present invention may utilize a mass-sensing technique, such as surface plasmon resonance. In addition, the biosensor may further employ a sensor chip, wherein the sensor chip comprises a free electron metal that includes a sensor surface, wherein the free electron metal is copper, silver, aluminum or gold. The sensor chip may further comprise a hydrogel coupled to the sensor surface, wherein the hydrogel has a plurality of functional groups, and wherein the one or more sensing surface-bound biomolecules are covalently bonded to the hydrogel.

In a more specific embodiment, a sensor surface adopted for use with a biosensor is disclosed. The sensor surface comprises a hydrogel matrix coating coupled to a top surface of the sensor surface, wherein the hydrogel matrix coating has plurality of functional groups. At least two different liposomes are bonded to the plurality of functional groups at discrete and noncontiguous locations on the hydrogel mixtrix coating of the sensor surface. In one embodiment, the sensor surface is a sensor chip, and a free electron metal is interposed between the hydrogel matrix and the top surface of the sensor surface.

In another embodiment of this invention, an apparatus is disclosed for assaying a drug candidate, wherein the apparatus comprises a biosensor having one or more sensing surface-bound biomolecules associated therewith and capable of measuring at least one binding interaction parameter of the drug candidate, and a computer memory containing a data structure for comparing the at least one binding interaction parameter against at least one mathematical expression correlated from binding interaction data associated with known drug compounds to determine an estimate of at least one pharnacokinetic parameter of the drug candidate.

In yet a further embodiment, a computer memory containing a data structure useful for assaying a drug candidate in accordance with the methods of the present invention is disclosed (as well as a generated data signal conveying the same). The data structure may be used to determine an estimate of at least pharmacokinetic parameter of the drug candidate.

These and other aspects of the present invention will be evident upon reference to the following detailed description and related Figures.

BRIEF DESCRIPTION OF THE DRAWINGS

FIG. 2A illustrates a single "dip" depicting the reflected light intensity associated with a homogeneous sensor surface.

FIG. 2B illustrates a number of "dips" depicting the non-averaged reflected light intensities associated with a non-homogeneous sensor surface.

FIG. 2C illustrates a broadening of the "dip" depicting the averaged reflected light intensities associated with a non-homogeneous sensor surface.

DETAILED DESCRIPTION OF THE INVENTION

Figure 1A:
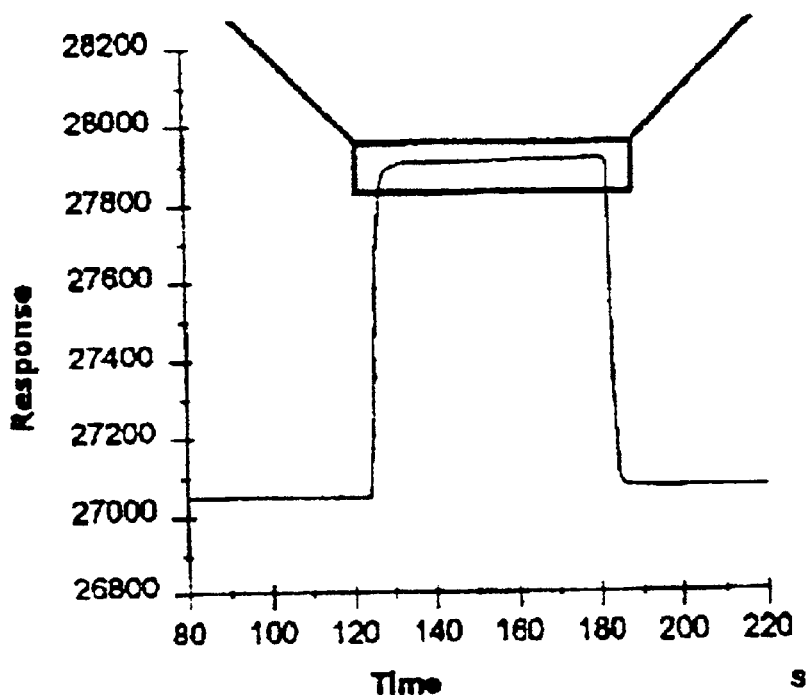
FIG. 1A illustrates a sensorgram reflective of the steady-state binding levels associated with a selected drug-biomolecule interaction.

The present invention is directed to a method for assaying a drug candidate and, more specifically, to a method and apparatus for measuring the binding interaction between at least one drug candidate and sensing surface-bound biomolecules of a biosensor to determine a binding interaction parameter of the drug candidate, and then comparing the binding interaction parameter against a predetermined drug correlation graph (e.g., a mathematical expression fitted to a series of known data points) to determine an estimate of at least one pharmacokinetic parameter. Although many specific details of certain embodiments of the invention are set forth in the following detailed description and accompanying Figures, those skilled in the art will recognize that the present invention may have additional embodiments, or that the invention may be practiced without several of the details described herein.

For purposes of clarity and to assist in understanding the full scope of the present invention, a brief review of the nomenclature associated with pharmacokinetics has been provided. As used within the context of the present invention, the following pharmacokinetic terms shall be construed broadly, and shall have their generally accepted meanings as set forth below. (As previously noted, "pharmacokinetics" refers to the study of the kinetics associated with the dynamic processes of absorption, distribution, metabolism, and excretion (ADME) of a drug and/or its metabolites within a living organism.)

"Absorption" refers to the process of uptake of a drug compound from the site of administration into the systemic circulation. The transfer of drug across the intestinal lumen is generally referred to as oral absorption, whereas the transfer of drug across an external physiological barrier is referred to general absorption. As disclosed herein, the pharmacokinetic parameter of absorption may be estimated from biosensor data associated with a sensor chip having, for example, a plurality of appropriate liposomes immobilized thereon.

"Distribution" refers to the transfer of a drug compound from the site of administration to the total systemic circulation and then to extracellular and intracellular water and tissues. Drug distribution is usually a rapid and reversible process. As disclosed herein, the pharmacokinetic parameter of distribution may be estimated from biosensor data associated with a sensor chip having, for example, a plurality of appropriate plasma proteins, liposomes, and/or transport proteins immobilized thereon.

"Metabolism" refers to the sum of all the chemical reactions for biotransformation of endogenous and exogenous substances which take place in the living cell. As disclosed herein, the pharmacokinetic parameter of metabolism may be estimated from biosensor data associated with a sensor chip having, for example, a plurality of appropriate metabolic enzymes immobilized thereon.

"Excretion" refers to the final elimination or loss of a drug from the body. Drug excretion includes both passive diffusion and relative specific carrier mediated excretion. Drugs may be excreted, unchanged or as metabolites, in urine via the kidneys or in feces via the bile and/or the intestine. Volatile compounds are often excreted in expired air by the lungs. As disclosed herein, the pharmacokinetic parameter of excretion may be estimated from biosensor data associated with a sensor chip having immobilized thereon, for example, an antibody that specifically detects the drug, as well as other proteins/receptors having a high affinity/specificity against the drug candidate. Such antibodies and proteins/receptors may be used to quantify the concentration/amount of the drug in different body fluids (e.g., urine/feces) and tissues, using a direct binding assay.

In addition to these ADME parameters, the solubility of a drug is also an important property that may be measured by the methods of the present invention. "Solubility" refers to the ability of two substances to form a homogeneous solution or mixture with each other. Solubility is important for the dissolution of drug given in solid dosage form. As disclosed herein, the solubility of a drug candidate may be estimated from sensorgram irregularities associated with reflectance minimum and dip-shape of biosensor data.

Furthermore, and as used herein, the term "parameter" refers to a constant or variable term in a function (e.g., a mathematical expression) that determines the specific form of the function but not necessarily its general nature. For example, the constant term "a" in the function f(x)=ax, where "a" determines only the slope of the line described by f(x), is referred to as a parameter. As such, the term "binding interaction parameter" refers to those constant or variable terms that are related to the binding interaction between a drug candidate and a sensing surface-bound biomolecule and includes, for example, association and dissociation rate constants, as well as maximum binding capacity. Similarly, the term "pharmacokinetic parameter" refers to those constant and variable terms that are related to the disposition of the drug candidate within a living organism and includes, for example: volume of distribution; total clearance; protein binding; tissue binding; metabolic clearance; renal clearance; hepatic clearance; biliary clearance; intestinal absorption; bioavailability; relative bioavailability; intrinsic clearance; mean residence time; maximum rate of metabolism; Michaelis-Menten constant; partitioning coefficients between tissues and blood (or plasma) such as those partitioning coefficients associated with the blood brain barrier, blood placenta barrier, blood human milk partitioning, blood adipose tissue partitioning, and blood muscle partitioning; fraction excreted unchanged in urine; fraction of drug systemically converted to metabolites; elimination rate constant; half-life; and secretion clearance.

The methods of the present invention are intended to be carried out by use of an affinity-based biosensor. As is appreciated by those skilled in the art, "biosensors" are analytical devices for analyzing minute quantities of sample solution having an analyte of interest, wherein the analyte is analyzed by a detection device that may employ a variety of detection methods. Typically, such methods include, but are not limited to, mass detection methods, such as piezoelectric, optical, thermo-optical and surface acoustic wave (SAW) device methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example, ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers.

In the detailed description and Examples that follow, the present invention is illustrated in the context of SPR spectroscopy. However, it is to be understood that the present invention is not limited to this detection method. Rather, any affinity-based detection method where an analyte binds to a ligand immobilized on a sensing surface may be employed, provided that a change in a property of the sensing surface is measured and quantitatively indicative of binding of the analyte to the immobilized ligand thereon. In the context of SPR spectroscopy, one exemplary class of biosensors is sold by Biacore AB (Uppsala, Sweden) under the tradename BIACORE® (hereinafter referred to as "the BIACORE instrument"). Such biosensors utilize a SPR based mass-sensing technique to provide a "real-time" binding interaction analysis between a surface bound ligand and an analyte of interest.

The BIACORE instrument includes a light emitting diode, a sensor chip covered with a thin gold film, an integrated fluid cartridge and a photo detector. Incoming light from the diode is reflected in the gold film and detected by the photo detector. At a certain angle of incidence ("the SPR angle"), a surface plasmon wave is set up in the gold layer, which is detected as an intensity loss or "dip" in the reflected light. More particularly, and as is appreciated by those skilled in the art, the phenomenon of surface plasmon resonance (SPR) associated with the BIACORE instrument is dependent on the resonant coupling of light, incident on a thin metal film, to oscillations of the conducting electrons, called plasmons, at the metal film surface. These oscillations give rise to an evanescent field which extends from the surface into the sample solution. When resonance occurs, the reflected light intensity drops at a sharply defined angle of incidence, the SPR angle, which is dependent on the refractive index within the reach of the evanescent field in the proximity of the metal surface.

Stated somewhat differently, surface plasmon resonance is an optical phenomenon arising in connection with total internal reflection of light at a metal film-liquid interface. Normally, light traveling through an optically denser medium, e.g., a glass prism, is totally reflected back into the prism when reaching an interface of an optically less dense medium, e.g., a buffer, provided that the angle of incidence is larger than the critical angle. This is known as total internal reflection. Although the light is totally reflected, a component of the incident light momentum called the evanescent wave penetrates a distance of the order of one wavelength into the buffer. The evanescent wave may be used to excite molecules close to the interface. If the light is monochromatic and p-polarized, and the interface between the media is coated with a thin (a fraction of the light wave-length) metal film, the evanescent wave under certain conditions will interact with free oscillating electrons (plasmons) in the metal film surface. When surface plasmon resonance occurs, light energy is lost to the metal film and the reflected light intensity is thus decreased.

The resonance phenomenon will only occur for light incident at a sharply defined angle which, when all else is kept constant, is dependent on the refractive index in the flowing buffer close to the surface. Changes in the refractive index out to about 1 μm from the metal film surface can thus be followed by continuous monitoring of the resonance angle. A detection volume is defined by the size of the illuminated area at the interface and the penetration depth of the evanescent field. It should be noted that no light passes through the detection volume (the optical device on one side of the metal film detects changes in the refractive index in the medium on the other side).

As noted above, the SPR angle depends on the refractive index of the medium close to the gold layer. In the BIACORE instrument, dextran is typically coupled to the gold surface, with the ligand being bound to the surface of the dextran layer. (Note a detailed discussion of matrix coatings for biosensor sensing surfaces is provided in U.S. Pat. No. 5,436,161, which is incorporated herein by reference in its entirety.) The analyte of interest is injected in solution form onto the sensor surface through the fluid cartridge. Because the refractive index in the proximity of the gold film depends upon (1) the refractive index of the solution (which is constant) and, (2) the amount of material bound to the surface, the binding interaction between the bound ligand and analyte can be monitored as a function of the change in SPR angle.

A typical output from the BIACORE instrument is a "sensorgram," which is a plot of response (measured in "resonance units" or "RU") as a function of time. An increase of 1,000 RU corresponds to an increase of mass on the sensor surface of approximately 1 $ng/mm^2$. As a sample containing the analyte contacts the sensor surface, the ligand bound to the sensor surface interacts with the analyte in a step referred to as "association." This step is indicated on the sensorgram by an increase in RU as the sample is initially brought into contact with the sensor surface. Conversely, "dissociation" normally occurs when sample flow is replaced by, for example, a buffer flow. This step is indicted on the sensorgram by a drop in RU over time as analyte dissociates from the surface-bound ligand. A detailed discussion of the technical aspects of the BIACORE instrument and the phenomenon of SPR may be found in U.S. Pat. No. 5,313,264, which is incorporated herein by reference in its entirety.

In addition, a detailed discussion of the technical aspects of the biosensor sensor chips used in connection with the BIACORE instrument may be found in U.S. Pat. No. 5,492,840, which is incorporated herein by reference in its entirety. This patent discloses, among other things, that each sensor chip may have a plurality of sensing surfaces, and that such sensing surfaces may be arranged in series or parallel with respect to the fluid sample pathway of the fluid cartridge. This patent also discloses that each of the plurality of sensing surfaces of a single sensor chip may have bound thereto a unique type of ligand that is capable of interacting with an analyte in its own characteristic way.

For example, and as disclosed herein, each of the four discrete sensing surfaces of the BIACORE instrument may have immobilized thereon biomolecules such as liposomes, plasma proteins, CYP 450 enzymes, other metabolic enzymes, and/or transport/efflux proteins. By immobilizing one or a selected combination of at least two different liposomes, plasma proteins, CYP 450 enzymes, other metabolic enzymes, and/or transport/efflux proteins, onto the one or more discrete sensing surfaces of a sensor chip, one or more pharmacokinetic parameters associated with a drug candidate may be readily determined. More specifically, and in one embodiment of the present invention, it has been discovered that (1) an estimate of an "absorption" parameter of a drug candidate may be determined from the binding interactions between the drug candidate and one or more appropriate liposomes; (2) an estimate of a "distribution" parameter of a drug candidate may be determined from the binding interactions between the drug candidate and an appropriate set of plasma proteins (e.g., specific and non-specific tissue binding and tissue permeability); (3) an estimate of a "metabolism" parameter of a drug candidate may be determined from the binding interactions between the drug candidate and an appropriate set of metabolic enzymes; and (4) an estimate of an "excretion" parameter of a drug candidate may be determined from the binding interactions between the drug candidate and an appropriate set of transport proteins.

Within the context of the present invention, suitable liposomes for estimating an "absorption" parameter of a drug candidate include organic compounds originating from natural or synthetic lipid molecules such as glycerophospholipids, glyceroglycolipids, sphingophospholipids and sphingoglycolipids, and from the classes phosphatidyl choline, phosphatidyl etanolamine, phosphatidyl serine, phosphatidyl glycerol, phosphatidyl acid, phosphatidyl inositol, galactopyranoside, digalactopyranoside, ceramide-phosphatidyl choline, ceramide-phosphatidyl etanolamine, ceramide-phosphatidyl serine, ceramide-phosphatidyl glycerol, ceramide-phosphatidyl acid, ceramide-phosphatidyl inositol, sphingomyelin molecules, glucosylceramides, glucocerebrosides, galactoceramides, galactocerebrosides, gangliosides, monoacyl phosphatidyl choline, cardiolipin molecules, that may be linked to saturated or unsaturated fatty or fluorocarbon chains ranging from eight to twenty-four carbons in length where fatty chains attached to the head group can be the same or of different structure, cholesterol, lanosterol, ergosterol, stigmasterol, sitosterol and derivatives thereof capable of being incorporated into lipid membranes, N,N-dimethyl-N-octadecyl-1-octadecanammonium chloride or bromide, (N-[1-(2,3-dioleoyloxy)propyl]-N,N,N-trimethylammonium chloride, diacetyl phosphate, N-[2,3-dihexadecyloxy)prop-1-yl]-N,N,N-trimethylammonium chloride, bolaamphiphiles, polyglycerolmonoalkylethers, polyethoxymonoalkylethers, as well as liposome-forming molecules from the classes amphiphilic polymers, amino acids, crown ether compounds and di(acyloxy) dialkylsilanes. The liposomes of the present invention and the like may be immobilized onto the sensing surface by the technique disclosed in Example 1.

Suitable plasma proteins for estimating a "distribution" parameter of a drug candidate include proteins such as Immunoglobulin G (7s-y-globulin), IgG; Immunoglobulin A, IgA; Secretory IgA, s IgA; Immunoglobulin M (19s-y-globulin) IgM; Immunoglobulin D, IgD; Immunoglobulin E, IgE; α1-Antitrypsin, α1Pl, a1 A; α1-Antichymotrypsin, (α1X-Glycoprotein) α1 X; Inter-α-Trypsin inhibitor, 1αTI; Antithrombin III, (heparin cofactor) AT III; α-Thiol Proteinase inhibitor (LMW kininogen) αTPI; C1-Inactivator, C1 esterase inhibitor (α2-neuraminoglycoprotein) C1INA: α2-Macroglobulin, α2 M; α2-Antiplasmin, α2AP; Cystatin C (Post-y-globulin; y-Trace protein); C1q (11S protein); C1r; C1s; C2; C3 (β1C-globulin), C4 (β1E-globulin); C5 (β1F-globulin); C6; C7; C8; C9; Factor B, (C3-proactivator; β2-glycoprotein II; glycine-rich β-glycoprotein); Factor D (C3-proactivator convertase); Properdin, P; Factor I, (C3b inactivator); C4-binding Protein; Fibrinogen, FI, Prothrombin, F II; Factor V (proaccelerin); FV; Factor VII, (proconvertin), F VII; Factor VIII: C (antihemophilic factor) F VIII: C; Factor VIII Related—Antigen; FV III: Rag (von Willebrand factor) (VWF); Factor IX (Christmas factor) F IX; Factor X, (Stuart-Power factor) F X; Factor XI (plasma thromboplalstin antecedent) F XI; Factor XII (Hageman factor) F XII; Factor XIII (fibrin stabilizing factor) F XIII; high-molecular-weight (HMW) Kininogen (Fitzgerald factor); Prekallikrein (Fletcher factor); Plasminogen; Protein C; Protein S; Allbumin, ALB; Haptoglobin, HP, Hp 1-1, Hp 2-1, Hp 2-2; Prealbumin (transthyretin, thyroxine-binding prealbumin); Retinol-binding Protein RBP; Thyroxine-binding Globulin TBG; Transcortin (corticosteroid-binding globulin) CBG; Sex hormone-binding globulin (Steroid-binding β Globulin) SHBG; Vitamin D-binding Protein (Gc-globulin, group specific component) VDBP; Transcobalamin I, TC I; Trancobalamin II, TC II; Transferrin (siderophilin) TF; Ferritin; Hemopexin, HPX; Apolipoprotein A, Apo A-1, Apo A-II; Apolipoprotein B, Apo B-48, Apo B-100; Apolipoprotein C; Apo C-I, Apo C-II, Apo C-III; Apolipoprotein E, Apo E; Apolipoprotein (a), apo (a); Serum Amyloid A, SAA; α-Fetoprotein, AFP; α1-Acid Glycoprotein (orosomucoid) α1 AG; Ceruloplasmin, CP; Serum Amyloid P protein (9.5S α1-glycoprotein; α1-macroglobulin) SAP; α2-HS Glycoprotein, α2 HS; Fibronectin (cold insoluble globulin) FN, C-reactive Protein, CRP; β2-microglobulin, β2 M; Pregnancy-specific β1-glycoprotein, SP1; α1-microglobulin, α1 M. The plasma proteins of the present invention and the like may be immobilized onto the sensing surface through the use of known immobilization techniques as is appreciated by those skilled in the art.

Suitable metabolic enzymes for estimating a "metabolism" parameter and/or an "excretion" parameter of a drug candidate include cytochrome P450-enzymes selected from the class of cytochrome P450 enzymes having an active site characterized by a protoporphyrin IX-iron complex with thiolate from a cysteine of the enzyme serving as the fifth ligand to iron. Suitable CYP 450 enzymes include CYTOCHROME P450, CYP1A1, CYP1A2, CYP2A1, 2A2, 2A3, 2A4, 2A5, 2A6, CYP2B1, 2B2, 2B3, 2B4, 2B5, 2B6, CYP2C1, 2C2, 2C3, 2C4, 2C5, 2C6, 2C7, 2C8, 2C9, 2C10, 2C11, 2C12, CYP2D1, 2D2, 2D3, 2D4, 2D5, 2D6, CYP2E1, CYP3A1, 3A2, 3A3, 3A4, 3A5, 3A7, CYP4A1, 4A2, 4A3, 4A4, CYP4A11, CYP P450 (TXAS), CYP P450 11A (P450scc), CYP P450 17(P45017a), CYP P450 19 (P450arom), CYP P450 51 (P45014a), CYP P450 105A1, CYP P450 105B1. Other important metabolic enzymes include Glutathione-thioethers, Leukotriene C4,butyrylcholinesterase, human serum paraoxonase/ arylesterase, N-Acetyltransferase, UDP-glucuronosyltransferase (UDPGT) isoenzymes, TL PST, TS PST, drug glucosidation conjugation enzyme, the glutathione-S-transferases (GSTs) (RX:glutathione-R-transferase), GST1, GST2, GST3, GST4, GST5, GST6, alcohol dehydrogenase (ADH), ADH I, ADH II, ADH III, aldehyde dehydrogenase (ALDH), cytosolic (ALDH1), mitochondrial (ALDH2), monoamine oxidase, MAO: Ec 1.4.3.4, MAOA, MAOB, flavin-containing monoamine oxidase, enzyme superoxide dismutase (SOD), Catalase, amidases, N1,-monoglutathionyl spermidine, N1,N8-bis (glutathionyl) spermidine, Thioesters, GS-SG, GS-S-cysteine, GS-S-cysteinylglycine, GS-S-O3H, GS-S-CoA, GS-S-proteins, S-carbonic anhydrase III, S-actin, Mercaptides, GS-Cu(I), GS-Cu(II)-SG, GS-SeH, GS-Se-SG, GS-Zn-R, GS-Cr-R, Cholin esterase, lysosomal carboxypeptidase, Calpains, Retinol dehydrogenase, Retinyl reductase, acyl-CoA retinol acyltrunderase, folate hydrolases, protein phosphates (pp) 4 st, PP-1, PP-2A, PP-2Bpp-2C, deamidase, carboxyesterase, Endopeptidases, Enterokinase, Neutral endopeptidase E.C.3.4.24. 11, Neutral endopeptidase, carboxypeptidases, dipeptidyl carboxypeptidase, also called peptidyl-dipeptidase A or angiotensin-converting enzyme (ACE) E.C.3.4.15.1, carboxypeptidase M, g-Glutamyl transpeptidase E.C.2.3.2.2, Carboxypeptidase P, Folate conjugase E.C.3.4.12.10, Dipeptidases, Glutathione dipeptidase, Membrane Gly-Leu peptidases, Zinc-stable Asp-leu dipeptidase, Enterocytic intracellular peptidases, Amino tripeptidase E.C.3.4.11.4, Aminodipeptidase E.C.3.4.13.2, Prodipeptidase, Arg-selective endoproteinase; the family of brush border hydrolases, Endopeptidase-24.11, Endopeptidase-2 (meprin), Dipeptidyl peptidase IV, Membrane dipeptidase GPI, Glycosidases, Sucrase-isomaltase, Lactase-glycosyl-ceraminidase, Glucoamylase-maltase, Trehalase, Carbohy-drase enzymes, alfa-Amylase (pancreatic), Disaccharidases (general), Lactase-phhlorizin hydrolase, Mammalian carbohydrases, Glucoamylase, Sucrase-Isomaltase, Lactase-glycosyl ceramidase, Enzymatic sources of ROM, Xanthine oxidase, NADPH oxidase, Amine oxidases, Aldehyde oxidase, Dihydroorotate dehydrogenase, Peroxidases, Human pancreatic exocrine enzymes, Trypsinogen 1, Trypsinogen 2, Trypsinogen 3, Chymotrypsinogen, proElastase 1, proElastase 2, Protcase E,Kallikreinogen, proCarboxypeptidase A1, proCarboxypeptidase A2, proCarboxypeptidase B 1, proCarboxypeptidase B2, Glycosidase, Amylase, lipases, Triglycaride lipase, Collipase, Carboxyl ester hydrolase, Phospholipase A2, Nucleases, Dnase I, Ribonucleotide reductase (RNRs), Wistar rat exocrine pancreatic proteins, Label Protein IEP, A1 Amylase 1, A2 Amylase 2, Lipase, CEL Carboxyl-ester lipase, PL Prophospholipase A, T1 Trypsinogen 1, T2 Trypsinogen 2, T3 Trypsinogen 3, T4 Trypsinogen 4, Cl Chymotrypsinogen 1, C2 Chymotrypsinogen 2, PE1 Proelastase 1, PE2 Proelastase 2, PCA Procarboxypeptidase A1, PCA1 Procarboxypeptidase A2, PCB1 Procarboxypeptidase B1, PCB2 Procarboxypeptidase B2, R Ribonuclease, LS Lithostatin, Characteristics of UDPGT isoenzymes purified from rat liver, 4-nitrophenol UDPGT, 17b-Hydroxysteriod UDDPGT, 3-a-Hydroxysteroid UDPGT, Morphine UDPGT, Billirubin UDPGT, Billirubin monoglucuronide, Phenol UDPGT, 5-Hydroxytryptamine UDPGT, Digitoxigenin monodigitoxide UDPGTC, 4-Hydroxybiphenyl UDPGT, Oestrone UDPGT, Peptidases, Aminopeptidase N, Aminopeptidase A, Aminopeptidase P, Dipeptidyl peptidase IV, b-Casomorphin, Angiotensin-converting enzyme, Carboxypeptidase P Angiotensin II, Endopeptidase-24.11, Endopeptidase-24.18 Angiotensin I, Substance P (deamidated), Exopeptidase,1. NH2 terminus Aminopeptidase N (EC 3.4.11.2), Aminopeptidase A (EC 3.4.11.7), Aminopeptidase P (EC 3.4.11.9), Aminopeptidase W (EC 3.4.11.-), Dipeptidyl peptidase IV (EC 3.4.14.5), g-Glutamyl transpeptidase (EC 2.3.2.2), 2. COOH terminus Anglotensin-converting enzyme (EC 3.4.15.1), Carboxypeptidase P (EC 3.4.17.-), Carboxypeptidase M (EC 3.4.17.12),3. Dipeptidase Microsomal dipeptidase (EC 3.4.13.19), Gly-Leu peptidase, Zinc stable peptidase, Endopeptidase Endopeptidase-24.11 (EC 3.4.24.11), Endopeptidase-2 (EC 3.4.24.18, PABA-peptide hydrolase, Meprin, Endopeptidase-3, Endopeptidase (EC 3.4.21.9), GST A1-1, Alpha,GST A2-2 Alpha, GST M1a-1a Mu, GST M1b-1b Mu, GST M2-2 Mu, GST M3-3 Mu, GST M4-4 Mu, GST M5-5 Mu, GST P1-1 Pi, GST T1-1 Theta, GST T2-2 Theta, Microsomal Leukotriene C4 synthase, UGT isozymes, UGT1.1, UGT1.6, UGT1.7, UGT2.4, UGT2.7, UGT2.11, Pancreatic enzymes, Elastase, Aminopeptidase (dipeptidyl aminopeptidase (IV), Chymotrypsin, Trypsin, Carboxypeptidase A, Methyltransferases, O-methyltransferases, N-methyltransferases, S-methyltransferases, Catechol-O-methyltransferases, MN-methyltransferase, S-sulphotransferases, $Mg^{2+}$-ATPase, Growth factor receptors Alkaline phosphatase, ATPases, Na, K+ATPase, $Ca^{2+}$-ATPase, Leucine aminopeptidase, K+channel. The metabolic enzymes of the present invention and the like may be immobilized onto the sensing surface through the use of known immobilization techniques as is appreciated by those skilled in the art.

Suitable transport proteins for estimating an "excretion" (as well as an efflux, absorption, distribution) parameter of a drug candidate include Glucose a. Na+-glucose cotransp GLUT 1, b. Facilitative transporter, GLUT 1-5, GLUT-2, Neutral amino acid transporter, Na+-independent system L amino acid transporter, cationic amino acid, Y+ cationic L-amino acid transporter, Dipeptides H+ contransport, Nucleosides Na+-dependent and facilitative, Taurine Na+ and Cl− dependent, Bile acids Na+/bile acid cotransporter, Na+-independent bile acid transporter, ABC transporters, Prostaglandins facilitative transpoprter, Na+/H+ exchanger Antiporter, Phosphate Na+/Pi cotransporter, Sulfate Na+-cotransporter, Transporters for neurotransmitters, Norepinephrine Na+/Cl− cotransporter, Dopamine Na+/Cl− cotransporter, Serotonine Na+/Cl− cotransporter, GABA, GAT-1, Na+/Cl dependent, Glycine Na+/Cl− dependent, Glutamate Na+ cotransporter, K+/OH− counter-transport, ABC transporters, P-glycoprotein (MDR1, MDR 2 OR MDR 3), Cl−- channel(CFTR), Antigenic peptides, TAP1 and TAP2 heterodimer, Lung resistance protein (LRP), Multidrug resistance protein 1 (MRP1), Multidrug resistance protein 2 (MRP2 or cMOAT), Multidrug resistance protein 3 (MRP3), Multidrug resistance protein 4 (MRP4), Multidrug resistance protein 5 (MRP5), Multidrug resistance protein 6 (MRP6), mrp (mouse), EBCR (rabbit), C. elegans mrpl (nematode), C. elegans mrp2 (nematode), MRP6 (human), YCF1 (yeast), AtMRP1 (Arabidopsis), SUR1 (human), sur2 (rat, mouse), YOR1/YRS1 (yeast), LtpgpA (leishmania), Hepatic amino acid transport system, Neutral amino acid transporters, MeAIB, Dicarboxylic amino acids, Neutral amino acids (branched), b-amino acids, Long chain fatty acids, Monoglycerides, L-Lysophosphatidylcholine, Transport proteins for bilirubin, Bilitranslocase (BTL), Organic anion binding protein (OABP), BSP/bilirubin binding protein, Signal receptor and transduction-hydrolases, ATPases, $Na^+$ dependent/independent bile acid transport, Bilirubin/BSP carrier (Cl-dependent), SO/OH exchanger $Cl^-$ channel $Na^+/H^+$ exchanger, $Na^+/HCO^3$ cotransport, GSH-, GSSH-, GS conjugate carrier, $SO^4/HCO^3$ exchanger, $Na^+$-dependent amino acid transport, Dipolar amino acid transporter, Basic amino acids, Cystine, Imino acids $Cl^-$, b-Amino acids $Cl^-$, XAG Acidic amino acids $K^+$, A Dipolar a-amino acids, three-and four-carbon dipolar amino acids, L Bulky, hydrophobic, dipolar amino acids, y+ Basic amino acids, folate transporter, cbl transport proteins, $Na^+$-$K^-$-ATPase, Bile acid transporter (BAT), protein kinase C, $Na^+/I^-$ sympoter (NIS); Bile salt export pump(BSEP, cBAT, SPGP); Intestinal bile acid transporters; Purine selective $Na^+$-dependent nucleoside transporter (hSPNTI); Pyrimidine selective $Na^+$-dependent nucleoside transporter (cNTI); Mitoxantrone transporter (MXR1 and MXR2); Intestinal oligopeptide transporter(PepT1); Renal oligopeptide transporter(PepT2), Breast cancer resistance protein (BCRP). The transport/efflux proteins of the present invention and the like may be immobilized onto the sensing surface through the use of known immobilization techniques as is appreciated by those skilled in the art.

As stated above, it has been discovered that the pharmacokinetic parameters of absorption, distribution, metabolism, and excretion (ADME) of a drug candidate may be determined from the binding interactions between the drug candidate and appropriate sensing surface-bound biomolecules (e.g, from different liposomes, plasma proteins, CYP 450 enzymes, other metabolic enzymes, and/or transport/efflux proteins, such as those as identified above) of a biosensor. That is, the binding interactions between a drug candidate and one or more sensing surface-bound biomolecules selected from liposomes, plasma proteins, CYP 450 enzymes, other metabolic enzymes, and transport/efflux proteins, may be measured via the BIACORE instrument to determine a "binding interaction parameter" of the drug candidate. The estimated binding interaction parameter may then, in turn, be compared against a predetermined drug correlation graph to estimate one or more absorption, distribution, metabolism, and excretion "pharmacokinetic parameters" of the drug candidate. Moreover, the pharmacokinetic parameter of the drug candidate may be, for example, selected from the group consisting of volume of distribution; total clearance; protein binding; tissue binding; metabolic clearance; renal clearance; hepatic clearance; biliary clearance; intestinal absorption; bioavailability; relative bioavailability; intrinsic clearance; mean residence time; maximum rate of metabolism; Michaelis-Menten constant; partitioning coefficients between tissues and blood (or plasma) such as those partitioning coefficients associated with the blood brain barrier, blood placenta barrier, blood human milk partitioning, blood adipose tissue partitioning, and blood muscle partitioning; fraction excreted unchanged in urine; fraction of drug systemically converted to metabolites; elimination rate constant; half-life; and secretion clearance; any one of which may be determined from appropriate sensorgrams of the selected drug-biomolecule interaction (alternatively, they may be determined by extracting score vectors with principal component analysis from digitalized interaction profiles, as well as other known multivariate methods).

For example, to estimate an apparent equilibrium constant between a drug candidate and selected sensing surface-bound biomolecules, the following procedure may be employed. First, a concentration series (e.g., 0, 20, 50, 100, 500, and 1,000 $\mu M$) of the drug candidate may be prepared, and sequentially injected into a biosensor having a sensor chip operatively associated therewith, wherein the sensor chip has a reference sensing surface and at least one sensing surface with surface-bound biomolecules. The relative responses at steady-state binding levels for each drug concentration level may then be measured. Because of bulk-refractive index contributions from solvent additives in the biosensor's running buffer, a correction factor may be calculated (via known calibration procedures) and applied to give corrected relative responses. The corrected relative responses for each drug concentration may then be mathematically evaluated as is appreciated by those skilled in the art to estimate the apparent equilibrium constant.

More specifically, the apparent equilibrium constant (KD) between the drug candidate and the selected sensing surface-bound biomolecules may be calculated by fitting the measured equilibrium ($R_{eq}$) data and known drug concentration (C) data to Equation (1):

$$R_{eq}=C*R_{max}/(C+KD)+\text{offset} \quad (1)$$

wherein $R_{max}$ is the maximum binding capacity of the sensing surface. Alternatively, the apparent equilibrium constant (KD) may be calculated from as little as two concentrations (i.e., C1 and C2) of the drug candidate by use of Equation (2):

$$KD=(R_{eqC1}/C1-R_{eqC2}/C2)/(R_{eqC2}-R_{eqC1}) \quad (2)$$

The estimated apparent equilibrium constant (KD) or binding level at a specific molar drug concentration may then, in turn, be compared against a predetermined drug correlation graph to estimate one or more absorption, distribution, metabolism, and excretion parameters of the drug candidate.

In the context of the present invention, a predetermined drug correlation graph refers to a mathematical expression or function that has been developed from binding interaction data associated with known drug compounds. For example, a correlation graph may be constructed wherein known binding interaction parameters (e.g., apparent equilibrium constants and/or binding levels at specific molar drug concentrations) for known compounds are plotted along the abscissa (i.e., the x-axis) and corresponding measured binding interaction parameters obtained via the biosensor are plotted along the ordinate (i.e., the y-axis), or vice versa. Stated somewhat differently, the correlation plot is a graphical representation of a mathematical expression that correlates known and measured affinity data.

By comparing the estimated binding interaction parameter obtained from the selected drug-biomolecule interaction against the mathematical expression (i.e., correlation graph) correlated from known and measured affinity data, it has been surprisingly discovered that an estimate of a pharmacokinetic ADME parameter related to the drug candidate may be accurately predicted. In addition, by immobilizing a selected combination of at least two different liposomes, plasma proteins, CYP 450 enzymes, other metabolic enzymes, and/or transport/efflux proteins, onto one or more discrete sensing surfaces of a sensor chip, it has been further surprisingly discovered that at least two pharmacokinetic parameters associated with a drug candidate may be readily determined. Moreover, by immobilizing a selected combination of different liposomes, plasma proteins, CYP 450 enzymes, other metabolic enzymes, and/or transport/efflux proteins, onto the sensing surfaces of biosensor, such as in a predetermined line of different spots of biomolecules, an ADME pattern or profile, such as a drug candidate characterization matrix, may be readily developed. Such ADME profiles are of great utility for purposes of drug screening.

In addition to determining one or more pharmacokinetic parameters by monitoring the refractive index changes of a biosensor as disclosed above, the solubility of a drug candidate may also be simultaneously determnined (together with the one or more pharmacokinetic parameters) by monitoring the minimum, maximum or centroid of the drug-biomolecule interaction signal (as is disclosed, for example, in PCT Publication No. WO 97/09618, which is incorporated herein by reference in its entirety). More specifically, the solubility of the drug candidate may be estimated/identified from irregularities, as well as from reflectance minimum ($R_{min}$) and dip-shape data, shown in the sensorgram of the drug-biomolecule interaction. In general, the concentration at which precipitation occurs is referred to as the solubility limit; this property may be important to measure because it may indicate that the drug candidate has an affinity greater than otherwise indicated.

Solubility problems of the drug candidate may be detected because insoluble particles (i.e., precipitates) tend to bind to sensing surface-bound biomolecules, thereby causing the sensing surface to be non-homogenous. (A homogenous surface has the same surface concentration throughout, whereas a non-homogenous surface has concentration disruptions.) A non-homogenous sensing surface actually measures several refractive indices, which are all averaged together in the biosensor's detector. These multiple measurements from a single, but non-homogenous sensing surface, tend to result in an increase in reflectance minimum and a broadening of the dip associated therewith.

Figure 1B:
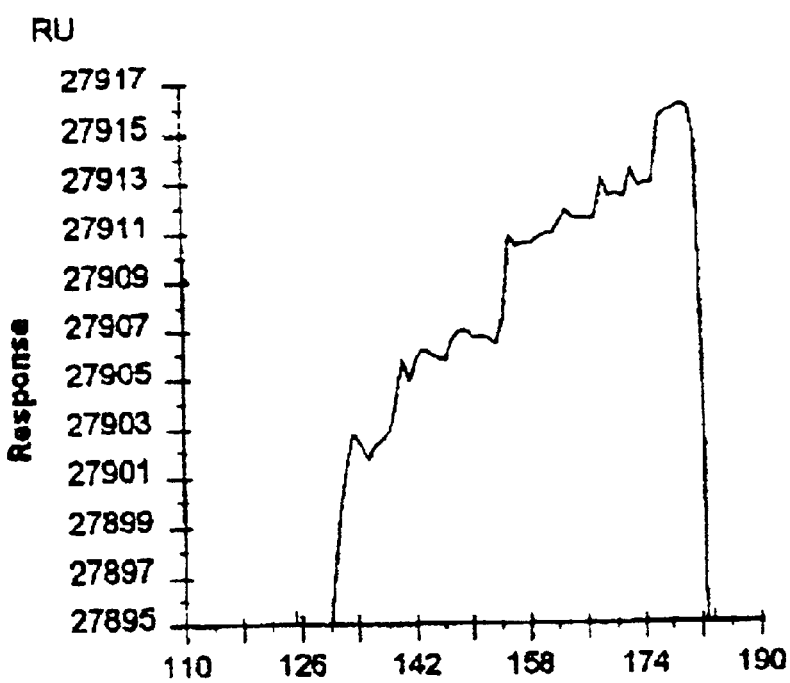
FIG. 1B illustrates an enlarged portion of the sensorgram of FIG. 1A and shows sensorgram irregularities.
Figure 1C:
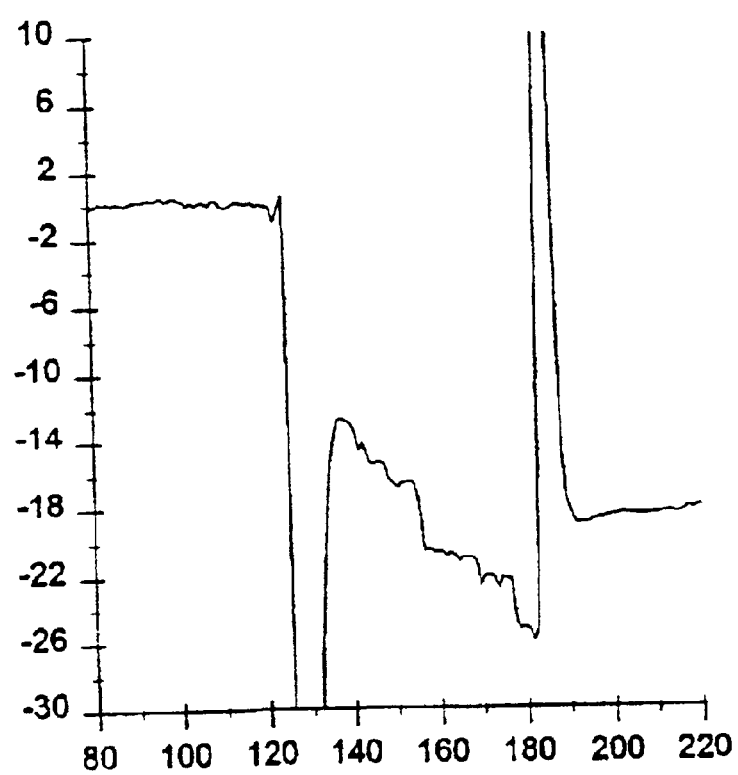
FIG. 1C illustrates an enlarged portion of the sensorgram of FIG. 1A, wherein bulk-refractive index effects have been eliminated.

An illustration of how sensorgram irregularities may be used to identify solubility problems (i.e., the presence of precipitates) is shown in FIGS. 1A–C. More specifically, the steady-state binding levels associated with a selected drug-biomolecule interaction is generally shown in FIG. 1A. By enlarging or "zooming" in on the top area of the sensorgram, which is reflective of the steady-state binding, the sensorgram irregularities become more apparent as is shown in corresponding FIG. 1B. The sensorgram irregularities become even more apparent by using reference subtracted data (i.e., bulk-refractive index effects have been eliminated) as is shown in corresponding FIG. 1C.

An illustration of how reflectance minimum ($R_{min}$) and dip-shape data may be used to identify solubility problems (i.e., the presence of precipitates) is shown in FIGS. 2A–C. More specifically, a homogeneous surface has the same surface concentration throughout, and will thus result in a single "dip" with respect to the reflected light intensity as shown in FIG. 2A. When precipitates bind to the sensing surface, the sensing surface becomes non-homogenous which tends to result in an increase in reflectance minimum and a broadening of the dip associated therewith as is shown in FIGS. 2B and 2C, respectively.

Based on the foregoing methods for assaying a drug candidate, researchers may now simultaneously measure several different pharmacokinetic parameters of the drug candidate, as well as gauge the drug candidate's solubility, by using a single analytical instrument. The present invention simplifies and improves the rate of drug discovery and development because important pharmacokinetic data may now be readily obtained at a relatively early stage of the process.

In addition to the foregoing methods, the present invention is also directed to apparatuses adapted to carrying out such methods. More specifically, the apparatuses of the present invention comprise a biosensor having a sensing surface associated therewith, and a computer system that facilitates the implementation of the steps associated with the methods disclosed herein. The computer includes a computer memory containing a data structure useful for assaying a drug candidate; the data structure comprises binding interaction data associated with known drug compounds such that the data structure may be used to determine an estimate of at least pharmacokinetic parameter of the drug candidate.

Figure 3:
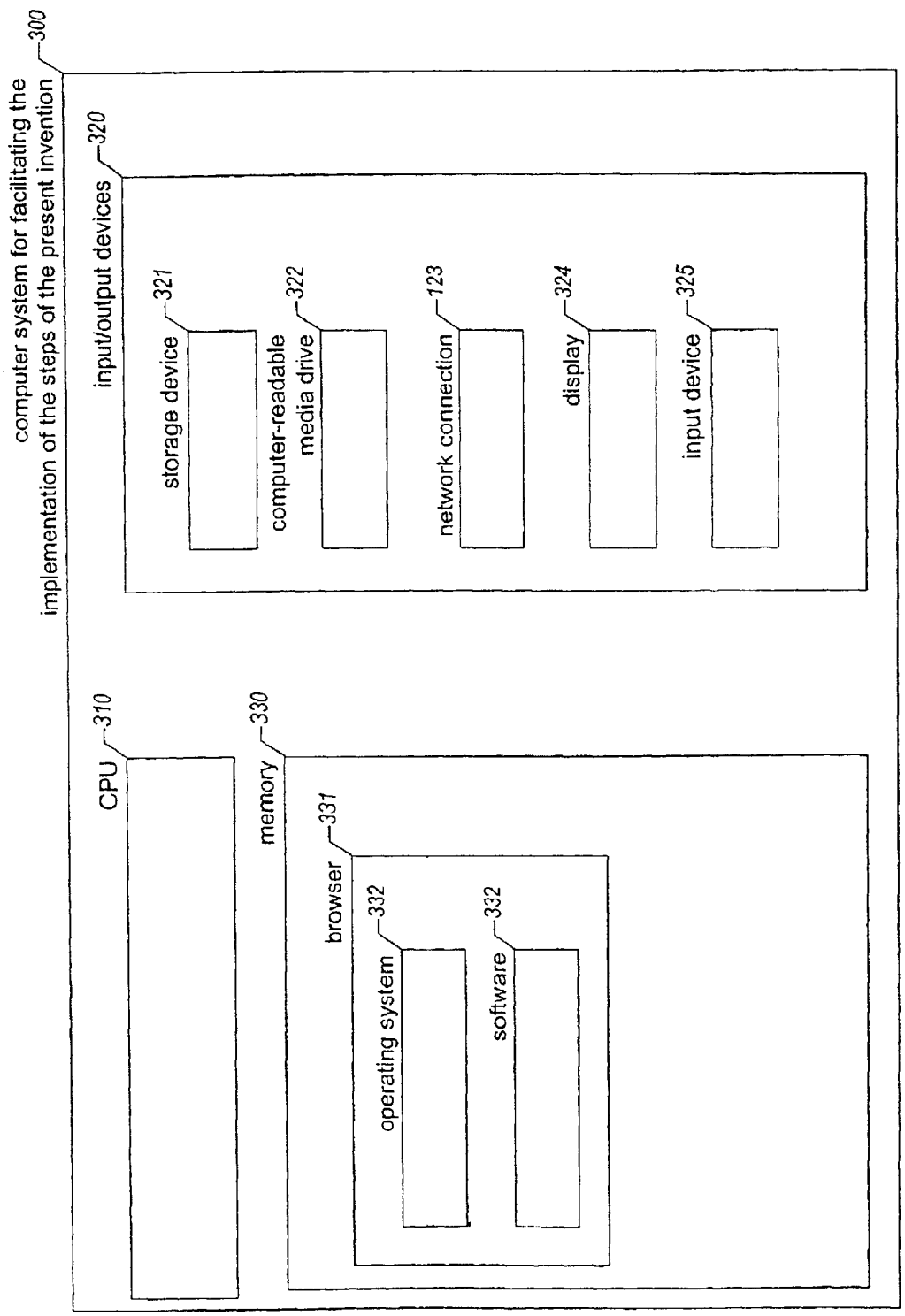
FIG. 3 shows a high-level block diagram of an exemplary computer system for assaying a drug candidate in accordance with the methods of the present invention.

The aspect of the present invention relating to a computer memory containing a data structure useful for assaying a drug candidate may be more fully illustrated in the context of a high-level computer block diagram as is depicted in FIG. 3. As shown, such a computer system 300 contains one or more central processing units (CPUs) 310, input/output devices 320, and the computer memory containing a data structure useful for assaying a drug candidate(memory) 330. Among the input/output devices is a storage device 321, such as a hard disk drive, and a computer-readable media drive 322, which may be used to install software products, where the software products are provided on a computer-readable medium, such as a CD-ROM. The input/output devices also include a network connection 323, through which the computer system 300 may communicate with other connected computer systems, such as networks. The input/output devices may also contain a display 324 and a data input device 325.

The memory 330 preferably contains an operating system 331, such as MICROSOFT WINDOWS, for providing to other programs access to resources of the computer system. The memory 330 preferably further contains software 332. While the computer memory containing a data structure useful for assaying a drug candidate is preferably implemented on a computer system configured as described above, those skilled in the art will recognize that it may also be implemented on computer systems having different configurations.

In a related aspect, the present invention is also directed to a generated data signal conveying a data structure useful for assaying a drug candidate. As above, the data structure comprises binding interaction data associated with known drug compounds, such that the data structure may be used to determine an estimate of at least pharmacokinetic parameter of the drug candidate.

In still a further embodiment, a sensor surface adapted for use with a biosensor is disclosed. The sensor surface has a hydrogel matrix coating coupled to the top surface of the sensor surface, wherein the hydrogel matrix coating has a plurality of functional groups, and at least two different types of liposomes are bonded to the plurality of functional groups at discrete and noncontiguous locations on the hydrogel matrix coating of the sensor surface (such as disclosed in Example 1). In the context of the BIACORE instrument as described above, the sensor surface is preferably in the form a sensor chip, wherein the sensor chip has a free electron metal interposed between the hydrogel matrix and the top surface of the sensor chip. Suitable free electron metals in this regard include copper, silver, aluminum and gold.

The sensor surface may have a lipophilic substance interposed between the different types of liposomes and the plurality of functional groups, wherein the lipophilic substance is covalently bonded to the plurality of functional groups. Representative lipophilic substances comprise an alkyl chain having from 12 to 24 carbon atoms, such as stearylamine. Similarly, representative liposomes include 1,2-dimyristol-sn-glycero-3-phosphocholine (DMPC) and 1-palmitoyl-2-oleoyl-sn-glycero-3-phosphocholine (POPC). The sensor surfaces of this invention may also have non-liposome biomolecules associated therewith. For example, human serum albumin, CYP 450 enzyme, a metabolic enzyme, and/or a transport protein may be bonded to the plurality of may be bonded to the plurality of functional groups at discrete and noncontiguous locations on the hydrogel matrix coating of the sensor surface.

For purposes of illustration and not limitation, the following examples more specifically disclose various aspects of the present invention.

EXAMPLES

Example 1

Simultaneous Measurement of Solubility, Plasma Protein Binding, Lipophilicity and Intestinal Absorption for Three Drug Candidates A–C This example discloses how combined information from each of four different flow-cells of a biosensor may be represented in a characterization matrix where each of the three drug candidates A–C illustrates a quality pattern (i.e., HSA % Bound, Predicted Lipophilicity, Solubility, and Predicted FA %) which is useful for the selection of lead drug compounds.
Preparation of Sensor Chip Three of the four discrete sensing surfaces of a CM5 Sensor Chip (Biacore AB, Uppsala, Sweden) were modified such that the CM5 Sensor Chip had surface-bound biomolecules as depicted below in Table 1.

TABLE 1

SURFACE-BOUND BIOMOLECULES OF CM5 SENSOR CHIP

| Surface/ Cell No. | Type of Flow-Cell | Surface Modification |
| --- | --- | --- |
| FC1 | Ref-1 | Unmodified carboxymethyl dextran (CM5) |
| FC2 | Target-1 | Human Serum albumin - HSA (9–12 kRU) |
| FC3 | Target-2 | DMPC-liposomes (5–7 kRU) captured on stearylamine |
| FC4 | Target-3 | POPC-liposomes (5–7 kRU) captured on stearylamine |

More specifically, and to achieve covalent attachment of stearylamine to surface/cell nos. 3 and 4, the following procedure was employed. A CM5 Sensor Chip was first inserted into a BIACORE 3000 biosensor (Biacore AB, Uppsala, Sweden). The flow of running buffer (isotonic phosphate buffer pH 7.0 (9.6 g $Na_2HPO_4$-$2H_2O$, 1.7 g $KH_2PO_4$, 4.1 g NaCl to 1 liter)) with 2% dimethylsulfoxide (DMSO) was directed to flow-cells 3 and 4 by using appropriate software commands. A mixture of 0.2 M N-ethyl-N'-(3-diethylaminopropyl)-carbodiimide and 50 mM N-hydroxysuccinimide in water was then injected into the biosensor so as to flow over flow-cells 3 and 4 for a period of 10 minutes. The CM5 Sensor Chip was then washed with running buffer, removed from the biosensor, and placed in a petri dish on top of a few layers of tissue paper that had been moistened with ethanol. The exposed sensing surfaces were then treated with 30 µl of a 10 mM stearylamine solution in 99% ethanol. After another 45 minute period, the CM5 sensor chip was gently washed with ethanol and then with water. Next, the exposed sensing surfaces were further treated with 50 µl of a 1M ethanolamine solution at pH 8.5. Finally, and after another 10 minute period, the sensing surfaces were washed with HBS-buffer.

Following covalent attachment of stearylamine to surface/cell nos. 3 and 4—and after the CM5 Sensor Chip that had just been washed with HBS-buffer was blown dry with nitrogen and reinserted into the biosensor—human serum albumin (HSA), DMPC-liposomes, and POPC-liposomes (available from Sigma) were then captured onto surface/cell nos. 2, 3 and 4, respectively. The following procedures were employed to capture these biomolecules.

To capture human serum albumin the flow was initially directed to flow-cell 2 by using appropriate software commands. The sensing surface of flow-cell 2 was then activated for a period of 7 minutes with EDC/NHS. Next, human serum albumin was injected at 15 µg/ml in 10 mM acetate buffer pH 5.2 for a period of 7 minutes; then 1M ethanolamine pH 8.5 was injected for another period of 7 minutes. This procedure resulted in the immobilization of 9–12 kRU of human serum albumin to the sensing surface of surface/cell no. 2.

To capture the two different liposomes the flow was first directed to flow-cell 3, and 0.5–1 mM DMPC liposome was injected until 5–7 kRU of the DMPC liposome had been captured. The flow was then directed to flow-cell 4, and 0.5–1 mM POPC liposome was injected until 5–7 kRU of the POPC liposome had been captured. Finally, the flow-system of the biosensor was washed with 100 mM NaOH, and the autoinjector tubing was washed with 0.5% SDS and 50 nM glycine pH 9.5 to remove trace lipids.
Calibration Procedure In order to improve data quality by reducing bulk-refractive index contributions from the DMSO solvent additive, a calibration procedure was employed. (Note the calibration procedure required varying concentrations of DMSO.) Because the running buffer contained 2% DMSO, a series of 8 to 10 calibration solutions were made that had varying DMSO concentrations ranging from 1.5% to 3.0%. Each calibration solution was sequentially injected over each of the four sensing surfaces by using the serial injection mode of the biosensor, and the respective steady-state binding levels were measured. The relative responses of the reference sensing surface of flow-cell 1 (FC1 having unmodified CM5 as a reference surface) were then subtracted from the corresponding calibration responses of the target sensing surfaces of flow-cells 2, 3, and 4, respectively, and plotted as functions of the relative responses. From these plots, calibration functions were calculated for each of the respective sensing surfaces.

The calibration functions were then used to calculate appropriate correction factors for the samples containing the three drug candidates A–C. That is, for the samples containing the drug candidates, the relative responses of the steady state binding levels of the reference sensing surface (i.e., signals from flow-cell 1) were measured and the respective calibration functions were used to calculate correction factors appropriate for each drug candidate. The correction factors were then applied (i.e., subtracted) to the differences between the reference responses and the sample responses to give a responses where the bulk-refractive index contributions from the DMSO solvent additive had been eliminated.
Corrected Relative Responses of Drug Candidates A–C The modified CM5 Sensor Chip (having surface-bound biomolecules as depicted above in Table 1) was used to measure the binding interaction of the three drug candidates A–C. Concentration series (i.e., 0, 20, 50, 100, 500, and 1,000 μM) of each drug candidate were prepared, and sequentially injected in serial mode into the biosensor such that four sensorgrams corresponding to each flow-cell were developed. Corrected relative responses at steady-state binding levels for each drug concentration were determined for each of the target sensing surfaces/flow-cells; such data is presented below in Tables 2–4.

TABLE 2

DRUG CONCENTRATION DATA FOR HUMAN SERUM ALBUMIN

| Candidate | 10 μM | 50 μM | 100 μM | 500 μM | 1,000 μM |
|---|---|---|---|---|---|
| A | 50 | 110 | 130 | 140 | 145 |
| B | 0 | 0 | 0 | 10 | 50 |
| C | 10 | 50 | 100 | 110 | 115 |

TABLE 3

DRUG CONCENTRATION DATA FOR POPC LIPOSOME

| Candidate | 10 μM | 50 μM | 100 μM | 500 μM | 1,000 μM |
|---|---|---|---|---|---|
| A | 10 | 300 | 400 | 450 | 500 |
| B | 0 | 0 | 40 | 60 | 70 |
| C | 0 | 0 | 0 | 0 | 10 |

TABLE 4

DRUG CONCENTRATION DATA FOR DMPC LIPOSOME

| Candidate | 10 μM | 50 μM | 100 μM | 500 μM | 1,000 μM |
|---|---|---|---|---|---|
| A | 0 | 50 | 70 | 90 | 95 |
| B | 0 | 10 | 20 | 50 | 55 |
| C | 0 | 0 | 0 | 0 | 0 |

Analysis of Data

The corrected relative responses for each drug concentration as depicted above in Tables 2–4 were, among other things, adjusted for differences in molecular weight of the drug candidates, as well as transformed to increase correlation with other properties. For example, for each target sensing surface/flow-cell, an apparent equilibrium constant (KD) was calculated by fitting the measured equilibrium ($R_{eq}$) data and known drug concentration (C) data to Equation (3):

$$R_{eq}=C*R_{max}/(C+KD)+\text{offset} \quad (3)$$

wherein $R_{max}$ is the maximum binding capacity of the sensing surface. In the fitting procedure, $R_{max}$, KD, and the offset were calculated.

Alternatively, the apparent equilibrium constant (KD) may have been calculated from two concentrations of the drug candidate, C1 and C2, by use of Equation (4):

$$KD=(R_{eqC1}/C1-R_{eqC2}/C2)/(R_{eqC2}-R_{eqC1}) \quad (4)$$

Figure 4:
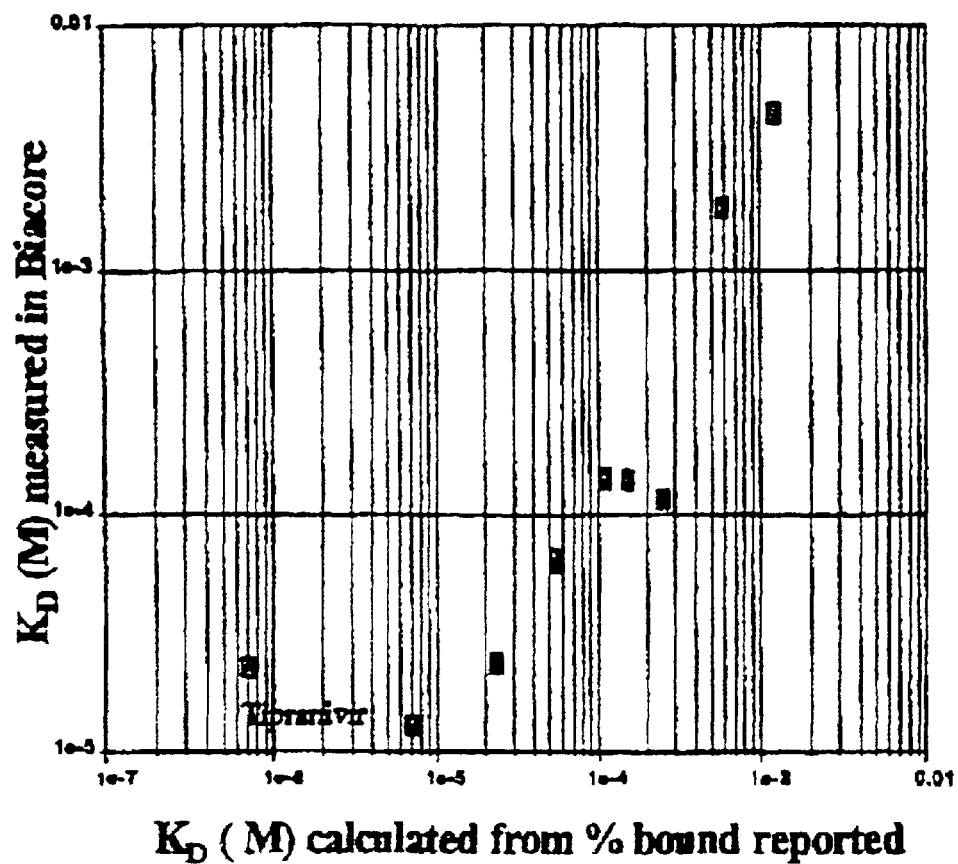
FIG. 4 depicts a correlation graph having known KD values for known compounds plotted along the abscissa (i.e., the x-axis) and corresponding measured KD values obtained via the biosensor plotted along the ordinate (i.e., the y-axis) for nine drugs with known levels of plasma protein binding

In either case, the KD values obtained via the biosensor were subsequently correlated with known KD values calculated from reported human serum albumin binding percentages (i.e., reported binding percentages that have been reported for known drug compounds), thereby enabling a prediction of the degree of protein binding for each of the three drug candidates A–C. In other words, a correlation graph as shown in FIG. 4 was constructed having known KD values for known compounds plotted along the abscissa (i.e., the x-axis) and corresponding measured KD values obtained via the biosensor plotted along the ordinate (i.e., the y-axis). This correlation graph was then used to predict the degree of plasma protein binding for each of the three drug candidates A–C (see below).

Figure 5:
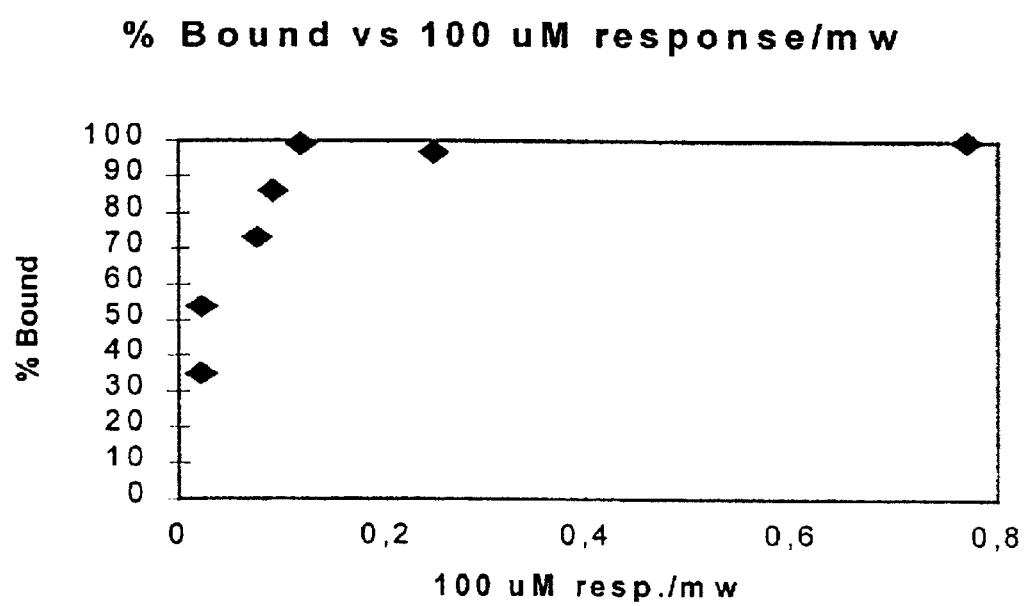
FIG. 5 depicts a correlation graph having respective binding levels at 100 $\mu$M (R 100 $\mu$M) divided by the molecular weight of known drug compounds' plotted along the abscissa (i.e., the x-axis) and corresponding human serum albumin binding percentage, as measured by equilibrium dialysis, plotted along the ordinate (i.e., the y-axis).

In addition, for each target sensing surface/flow-cell, a molecular weight adjusted response at a single concentration level was used as a threshold value for ranking the drug candidates A–C. More specifically, a correlation graph as shown in FIG. 5 was constructed, wherein respective binding levels at 100 μM (R 100 μM) divided by the known drug compounds' molecular weight were plotted along the abscissa (i.e., the x-axis) and corresponding human serum albumin binding percentage, as measured by equilibrium dialysis, were plotted along the ordinate (i.e., the y-axis). This correlation graph was then used to discriminate between strong and weak human serum albumin binders for each of the three drug candidates A–C.

Figure 6:
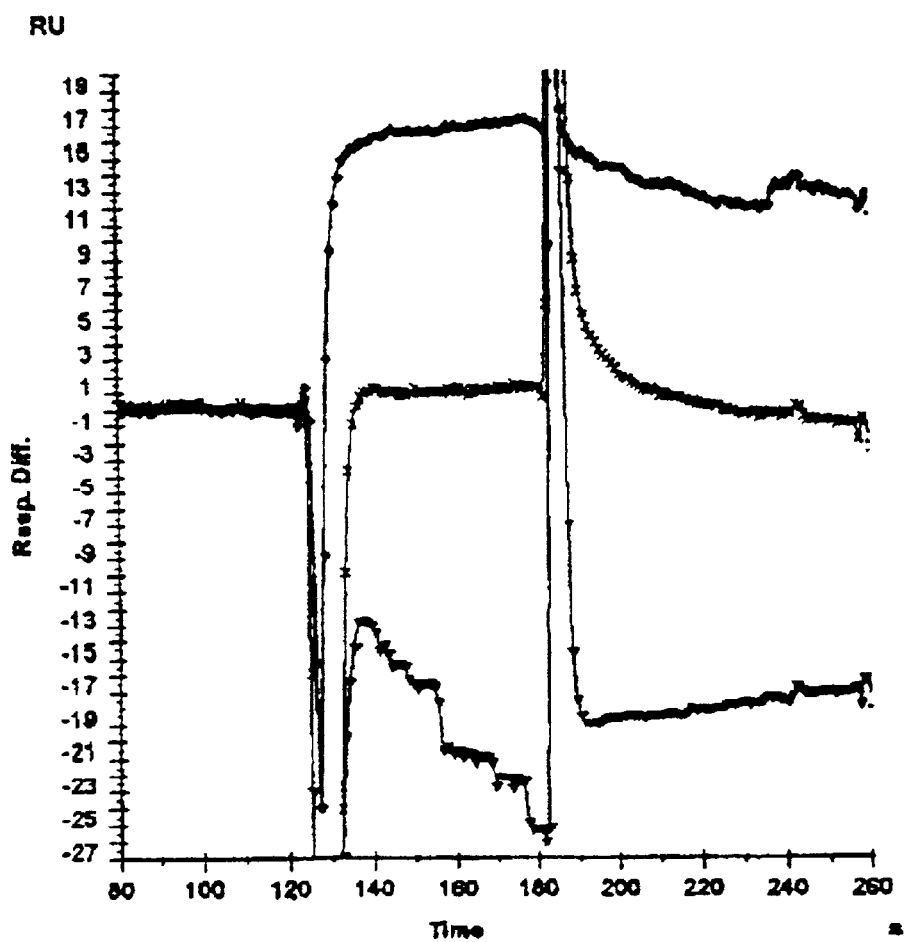
FIG. 6 depicts reference subtracted sensorgram traces for each of three drug candidates A–C.

Furthermore, for each target sensing surface/flow-cell, reference subtracted sensorgram traces (e.g., FC2 minus FC1) were developed to detect the presence of precipitates (caused by low solubility). More specifically, reference subtracted sensorgram traces for each of the three drug candidates A–C, as shown in FIG. 6, were constructed. (Note that when precipitates form and then bind/associate with the sensing surface, the response signal will decrease in a non-continuous way.) By analyzing the concentration series for each of the three drug candidates A–C (as shown in FIG. 6), it was determined that drug candidate A precipitated and thus had relatively low solubility, whereas drug candidates B–C did not precipitate and thus had relatively high solubilities.

Finally, and as shown below in Table 5, the combined information from each target sensing surface/flow cell was tabulated into a reduced characterization matrix where each drug candidate A–C received a quality pattern that was useful for selection of the lead drug compounds. (Note that the predicted lipophilicity and fraction absorbed are prophetic.)

TABLE 5

CHARACTERIZATION MATRIX FOR DRUG CANDIDATES A–C

| Candidate | HSA % Bound | Pred. Lipophilicity | Solubility | Predicted FA % |
|---|---|---|---|---|
| A | 99.9 | 4 | <1 μM | >97 |
| B | <90 | 2 | OK | >90 |
| C | >90 | −2 | OK | <50 |

Based on the forgoing characterization matrix, it was determined that drug candidate B was the preferred compound due to its low plasma protein binding level (HSA % bound <90), medium lipophilicity (predicted lipophilicity= 2), no identified solubility problems (solubility=OK), and acceptable intestinal absorption (predicted fraction absorbed >90).

Example 2

Demonstrated Correlation between Biosensor Data and Fraction Absorbed in Humans (FA %)

Figure 7:
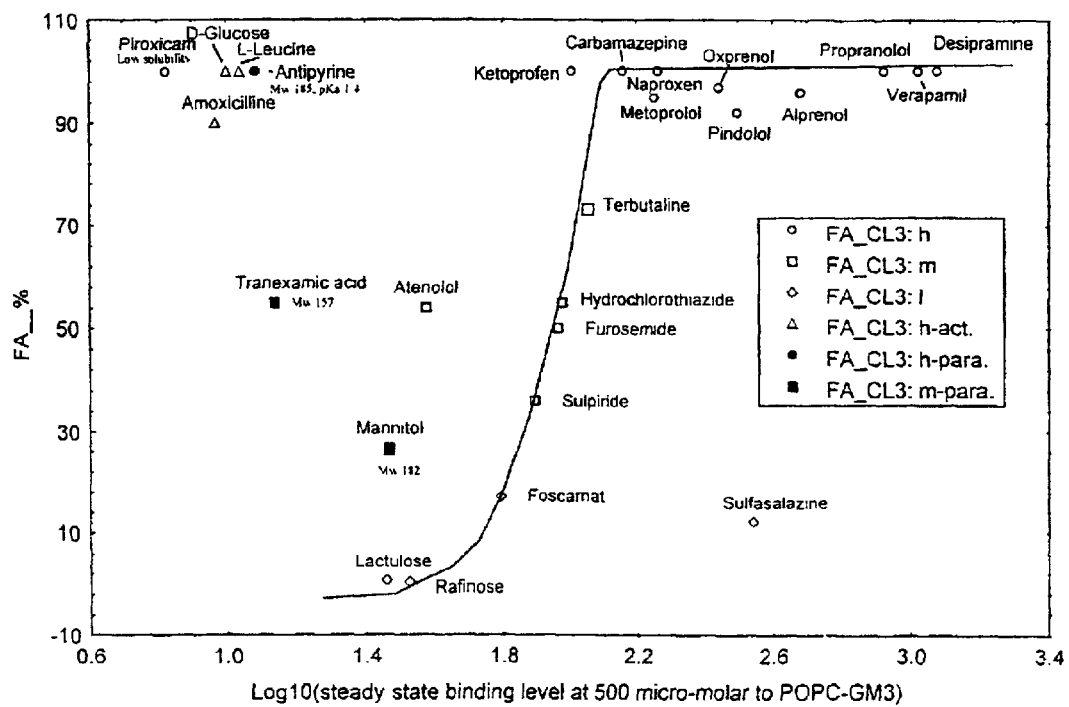
FIG. 7 depicts a correlation graph having known fraction absorbed in humans (FA%) plotted along the ordinate (i.e., the y-axis) and corresponding calibrated (i.e., reference subtracted) steady state binding levels for each drug at 500 $\mu$M plotted along the abscissa in a 10-logarithm scale (i.e., the x-axis).

This example discloses a correlation between biosensor data obtained form the BIACORE instrument (i.e., BIACORE 3000) and known data for the fraction absorbed in humans (FA %) for a number of different drugs, wherein the correlation graph is useful for drug candidate absorption predictions. More specifically, a correlation graph as shown in FIG. 7 was constructed having known fraction absorbed in humans (FA %) plotted along the ordinate (i e., the y-axis) and corresponding calibrated (i.e., reference subtracted) steady state binding levels for each drug at 500 $\mu$M plotted along the abscissa in a 10-logarithm scale (i.e., the x-axis). In this example, the sensing surfaces of the target flow-cells each had 6,000 RU of POPC-GM3 ganglioside (available from Sigma) captured on stearylamine tiles. (Note that an unmodified sensing surface of a CM5 Sensor Chip was used as the reference.) As shown in FIG. 7, there is high degree of correlation between the biosensor data and the known fraction absorbed in humans (FA %) data, as is evidenced by the mathematical expression/function that has been fitted to the various data points.

Moreover, the correlation graph also shows a classification of the various substances, wherein absorption of the substances using the passively transported trans-cellular route through the intestine are depicted by h=high, m=medium, and l=low, and wherein absorption using active transport is depicted by h-act=high, and wherein absorption of substances with molecular weights<200 using the paracellular route is depicted by h-para=high and m-para=medium, respectively. (Note the Sulfasalazine is a pre-drug which rapidly decomposes in the intestine, which may explain its outlier properties; Piroxicam has a very low solubility <<<<500 $\mu$M, which may explain its lack of correlation.)

While the present invention has been described in the context of the embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is, therefore, indicated by the appended claims rather than by the foregoing description, and all changes that come within the meaning and range of equivalency of the claims are to be embraced within their scope.

What is claimed is:

1. A method for assaying a drug candidate with a biosensor having one or more sensing surface-bound biomolecules associated therewith, comprising the steps of:
   measuring the binding interaction between the drug candidate and the one or more sensing surface-bound biomolecules of the biosensor to obtain at least one binding interaction parameter of the drug candidate related to the binding interaction between the drug candidate and the one or more sensing surface biomolecules; and
   comparing the at least one binding interaction parameter against at least one mathematical expression correlating binding interaction data measured for known drug compounds and known pharmocokinetic data for the drug compounds to determine an estimate of at least one pharmacokinetic parameter of the drug candidate.

2. The method of claim 1 wherein the at least one pharmacokinetic parameter is an absorption parameter, a distribution parameter, a metabolism parameter, or an excretion parameter.

3. The method of claim 1 wherein the at least one pharmacokinetic parameter is volume of distribution, total clearance, protein binding, tissue binding, metabolic clearance, renal clearance, hepatic clearance, biliary clearance, intestinal absorption, bioavailability, relative bioavailability, intrinsic clearance, mean residence time, maximum rate of metabolism, Michaelis-Menten constant, partitioning coefficients between tissues and blood or plasma, fraction excreted unchanged in urine, fraction of drug systemically converted to metabolites, elimination rate constant, half-life, or secretion clearance.

4. The method of claim 3 wherein the partitioning coefficients between tissues and blood or plasma are partitioning coefficients associated with the blood brain barrier, blood placenta barrier, blood human milk partitioning, blood adipose tissue partitioning, or blood muscle partitioning.

5. The method of claim 1 wherein an estimate of at least two pharmacokinetic parameters of the drug candidate are determined.

6. The method of claim 1 further comprising determining an estimate of a solubility property of the drug candidate.

7. The method of claim 1 wherein the biosensor utilizes a mass-sensing technique.

8. The method of claim 7 wherein the mass-sensing technique involves surface plasmon resonance.

9. The method of claim 1 wherein the at least one mathematical expression correlated from binding interaction data associated with known drug compounds is a function fitted to a plurality of data points plotted on a Cartesian coordinate system.

10. The method of claim 1 wherein the plurality of sensing surface-bound biomolecules are selected from liposonies, plasma proteins, CYP 450 enzymes, metabolic enzymes, or transport proteins.

11. The method of claim 1 wherein the biosensor utilizes a sensor chip comprising:
    a hydrogel coupled to the sensor surface, wherein the hydrogel has a plurality of functional groups, and wherein the one or more sensing surface-bound biomolecules are bonded to the hydrogel.

12. The method of claim 11 wherein the sensor chip further comprises:
    a free electron metal that includes a sensor surface, wherein the free electron metal is selected from the group consisting of copper, silver, aluminum and gold.

13. The method of claim 12 wherein the biosensor is capable of detecting surface plasmon resonance associated with the free electron metal.

14. The method of claim 12 wherein the hydrogel is a polysaccharide or a water-swellable organic polymer.

15. The method of claim 14 wherein the polysaccharide is dextran.

16. The method of claim 11 wherein the plurality of functional groups of the hydrogel of the sensor chip include one or more of a hydroxyl, carboxyl, amino, aldehyde, carbonyl, epoxy or vinyl functional group.

17. The method of claim 11 wherein the step of measuring comprises detecting a signal associated with a reflected light beam with respect to time, wherein the reflected light beam establishes a surface plasmon resonance with the free electron metal.

18. The method of claim 17 wherein the signal associated with the reflected light beam defines a resonance curve of the surface plasmon resonance.

19. The method of claim 17 wherein the signal associated with the reflected light beam defines a reflectance minimum of the surface plasmon resonance.

* * * * *

UNITED STATES PATENT AND TRADEMARK OFFICE
CERTIFICATE OF CORRECTION

PATENT NO. : 6,808,938 B2
DATED : October 26, 2004
INVENTOR(S) : Markku Hämäläinen It is certified that error appears in the above-identified patent and that said Letters Patent is hereby corrected as shown below:

Column 22,
Line 29, "liposonies" should read as -- liposomes --.

Signed and Sealed this

Twenty-third Day of August, 2005

JON W. DUDAS
*Director of the United States Patent and Trademark Office*